United States Patent [19]

Kipling et al.

[11] Patent Number: 5,374,521
[45] Date of Patent: Dec. 20, 1994

[54] ACOUSTIC REFLECTION PROCESS FOR MOLECULAR SENSING USING A BULK ACOUSTIC WAVE QUARTZ SENSOR

[76] Inventors: Arlin L. Kipling, 5601 Bradford Place, Montreal, Quebec, Canada, H3W 2M6; Michael Thompson, 1824 Delaney Drive, Mississauga, Ontario, Canada, L5J 3L1

[21] Appl. No.: 761,272

[22] Filed: Sep. 17, 1991

[51] Int. Cl.$^5$ ............... G01N 33/551; G01N 33/553
[52] U.S. Cl. ............................ 435/6; 73/587; 73/590; 73/645; 73/649; 310/312; 436/524; 436/527; 436/806; 422/82.01
[58] Field of Search ............... 73/587, 590, 618, 620, 73/627, 645, 649; 435/6; 436/524, 527, 806; 310/312; 422/82.01

[56] References Cited

U.S. PATENT DOCUMENTS

| | | | |
|---|---|---|---|
| 3,946,256 | 3/1976 | Day et al. | 73/587 |
| 4,242,096 | 12/1980 | Oliveira et al. | 436/513 |
| 4,314,821 | 2/1982 | Rice | 436/806 |
| 4,691,714 | 9/1987 | Wong et al. | 73/570 |
| 4,735,906 | 4/1988 | Bastiaans | 436/527 |
| 4,847,193 | 7/1989 | Richards et al. | 436/501 |
| 4,905,701 | 3/1990 | Cornelius | 436/806 |

Primary Examiner—Toni R. Scheiner
Assistant Examiner—Christopher L. Chin
Attorney, Agent, or Firm—Basile and Hanlon

[57] ABSTRACT

A passive process for selectively sensing analyte molecules in a fluid by reflection of acoustic waves from a sensing surface of a bulk accoustive wave quartz sensing device to which analyte molecules bind is provided. The sensing surface has a plurality of receptors for which analyte molecules have an affinity. The process has the following steps:

i) contacting a fluid in which analyte molecules are suspected with the sensing surface so that acoustic waves are reflected from the sensing surface;

ii) directing acoustic waves at the sensing surface; and iii) detecting a change in a characteristic of acoustic waves reflected from the sensing surface due to analyte molecules binding the receptors. The change in a reflected acoustic wave characteristic being measured by electrical means detecting values which are related to the amplitude and phase of the reflected acoustic waves.

12 Claims, 2 Drawing Sheets

ACOUSTIC REFLECTION PROCESS FOR MOLECULAR SENSING USING A BULK ACOUSTIC WAVE QUARTZ SENSOR

FIELD OF THE INVENTION

This invention relates to a process of sensing the concentration of specific molecules in a fluid, that is, a liquid or gas, by electrical measurements using a bulk acoustic wave (BAW) quartz sensor. The molecules to be sensed, called the analyte, bind specifically to molecules on the surface of the sensor, called the receptor. Acoustic waves generated in the interior of the sensor are partially reflected from the surface of the sensor. The reflected waves change as the analyte binds to the receptor and this change is detected by means of electrical measurements.

This invention further relates to applications of the acoustic reflection process for sensing biomolecules in general. An example of the application of the process is the sensing of a specific DNA molecule in which case the receptor-analyte molecules are complementary strands of DNA. Other examples of applications of the process are the sensing of drug-receptor interactions and sensing of immunochemical reactions.

BACKGROUND OF THE INVENTION

There are basically two types of processes which can be used to sense the concentration of specific molecules in a liquid using a BAW quartz sensor. The two types of processes may be called by the generic names, active and passive. The active method is more descriptively and commonly called the oscillator method. In this method the BAW quartz sensor is part of an oscillator circuit. It is connected between the output and input of the oscillator amplifier and thereby provides positive feedback that causes oscillation of the circuit. The resonant frequency of the circuit is measured by an electronic counter. The quartz sensor is itself active in the sense that it is continuously controlling the frequency of oscillation of the circuit. The oscillator method is inadequate when used to sense molecules in a liquid.

The acoustic reflection process is a passive method in which the BAW quartz sensor is connected externally to an instrument which applies voltages, which typically vary sinusoidally with time, across the terminals of the sensor. Signal voltages are measured at various frequencies of the applied voltage. The quartz sensor does not determine the frequency at which measurements are made and in that sense the sensor itself is passive. The acoustic reflection process does not have the disadvantages of the oscillator method. Therefore, this invention displaces the oscillator method.

The oscillator method has at least three limitations when used to sense molecules in a liquid. Only one electrical quantity is measured and so the characterization of the sensor is incomplete. The measured quantity is a frequency which is ideally the series resonant frequency, defined as the lower of the two frequencies for which the phase of impedance of the sensor is zero. However, rarely is the measured frequency the same as the series resonant frequency due to unknown phase shifts elsewhere in the oscillator circuit; this is the second limitation. Thirdly, the oscillator method can be used only when the sensor is in liquids of low viscosity.

The acoustic reflection process completely characterizes a bulk acoustic wave quartz sensor. This is achieved by making measurements over the complete frequency spectrum of the resonant region of the quartz sensor. The process can be used with the sensor in a liquid of any viscosity.

SUMMARY OF THE INVENTION

In accordance with an aspect of the invention, a passive process for specifically sensing analyte molecules in a fluid by reflection of bulk acoustic waves from a sensing surface of a bulk acoustic wave quartz sensing device to which analyte molecules bind, said sensing surface having a plurality of receptors for which analyte molecules have an affinity, said process comprises:

i) contacting a fluid in which analyte molecules are suspected with said sensing surface;

ii) directing acoustic waves at said sensing surface whereby acoustic waves are reflected from said sensing surface;

iii) detecting a change in a characteristic of acoustic waves reflected from said sensing surface due to analyte molecules binding said receptors said change in a reflected acoustic wave characteristic being measured by electrical means detecting values which are related to the amplitude and phase of the reflected acoustic waves.

BRIEF DESCRIPTION OF THE DRAWINGS

Preferred embodiments of the invention are shown in the drawings wherein.

DETAILED DESCRIPTION OF THE PREFERRED EMBODIMENTS

This invention relates to chemical sensors and biosensors in a liquid or gas which are sensing devices known as a bulk acoustic wave quartz sensors. This sensing device is a piezoelectric quartz crystal, used for control of frequency in electronic circuits, which has been modified. The sensing device is described first and then the process of molecular sensing is described.

Figure 1:
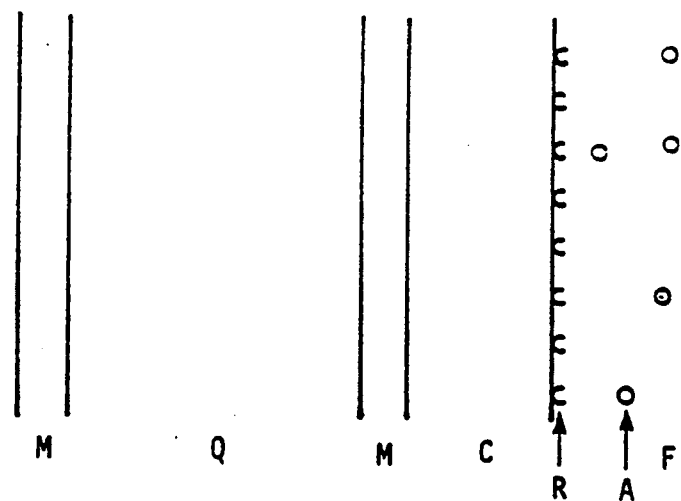
FIG. 1 is a schematic representation of the sensing device having a layered construction.

The structure of the sensing device is shown in FIG. 1, which is a side view of the device not drawn to scale. The unmodified piezoelectric quartz crystal is a thin plate of quartz, region Q in FIG. 1, and much thinner metal layers, called electrodes, deposited on each face of the quartz, regions M in FIG. 1. The quartz crystal is modified by attaching a coating, region C, to either one electrode as shown in FIG. 1, or to both electrodes. The coating, C, consists in general of more than one layer; the layers are not shown in the figure. The receptor, region R in FIG. 1, is attached to the surface of the coating. The receptor is a layer of molecules represented by half circles in FIG. 1 which bind specifically to the molecules to be sensed. The function of the coating is to immobilize the receptor on the surface of the sensor. The coating is not needed if the receptor can be attached directly to the metal electrode. The regions MQMCR in FIG. 1 constitute the modified piezoelectric quartz crystal, which will be henceforth called the sensor. If the coating is attached to both electrodes then the receptor is attached to both coatings and the regions RCMQMCR constitute the sensor.

A fluid (liquid or gas), region F in FIG. 1, is in contact with the surface of the sensor or the fluid is in contact with both surfaces of the sensor. The fluid contains the analyte, A, which is the assembly of molecules to be sensed. The analyte binds chemically or physically to the receptor. The analyte is represented in FIG. 1 by small circles and is shown before any of the analyte has combined with the receptor. As the analyte accumulates on the surface of the sensor, the properties of the surface change. In addition, the properties of the fluid very near the surface may also change. So in general the fluid is divided into two regions: the interfacial region which is very near to the surface of the sensor and the bulk region which is the rest of the fluid. The interfacial region is distinct from the bulk region when the fluid in the interfacial region has one or more properties which are different from the fluid in the bulk region. The interfacial region may consist of more than one layer of fluid, each layer of which has one or more properties different from the other layers and from the bulk region. The interfacial and bulk regions are not shown separately in FIG. 1.

The invention is the process of molecular sensing which detects the accumulation of the analyte on the surface of the sensor. A voltage is applied between the two metal electrodes, regions M in FIG. 1. The voltage can vary periodically with time or it can be a voltage step or a voltage pulse. The voltage of choice is a periodic voltage with a sinusoidal waveform and the process will be described in terms of this voltage, where hereafter the word voltage refers to sinusoidal voltage. The voltage is applied at one or more different frequencies over the resonant region of the quartz sensor.

The voltage at each frequency produces an electromagnetic field in the quartz which, in turn, produces acoustic waves in the quartz by the piezoelectric effect. The electromagnetic field is confined to the quartz by the metal electrodes. But part of the acoustic waves will flow out of the quartz and reach the receptor layer, R in FIG. 1. Part of the acoustic waves incident on the receptor layer will be reflected and return to the quartz where they will alter the electromagnetic field due to the piezoelectric effect. This in turn will change the electrical measurements made at the terminals of the sensor.

The magnitude and phase of the acoustic waves which are reflected from the receptor layer, R, and which return to the quartz depend on the amount of analyte which is bound to the receptor, which is related to the concentration of analyte in the fluid, and therefore the reflected acoustic waves carry that information back to the quartz. The interfacial region of the fluid may also change as the analyte binds to the receptor and that will change the reflected waves which return to the quartz. But the cause of the change of properties of both the sensor-fluid interface and the interfacial region of the fluid is the same: the binding of the analyte to the receptor. Therefore the change of reflected waves is due to one primary cause, the presence of the molecules to be sensed in the fluid.

The details of the process of molecular sensing can be described as follows. During the period of time when the analyte binds to the receptor, region C and both regions M will not change; only the properties of the surface of C, consisting of the receptor and that part of the analyte which is bound to the receptor, and perhaps the properties of a thin region of fluid adjacent to the surface of region C, with thickness from one to several monolayers of fluid molecules, will change. Therefore M and C can be considered as a single composite layer, denoted by L in FIG. 2. The other metal layer is not shown in FIG. 2 because its effect on the acoustic waves in Q will remain constant during the process of molecular sensing.

Figure 2:
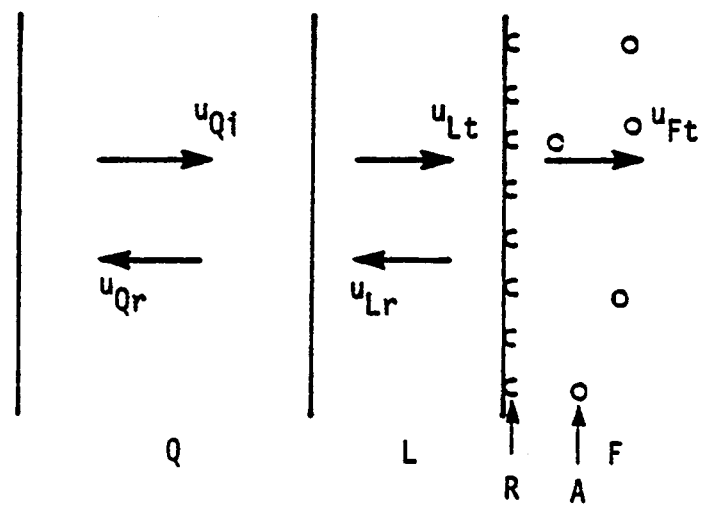
FIG. 2 is a schematic of the reflection of bulk acoustic waves within the sensing device.

There will be multiple reflections of the acoustic waves in region L of FIG. 2. After a sufficient number of transits of the acoustic waves in L, conditions in L will reach a steady state such that the rate at which acoustic energy is transmitted back into region Q plus the rate at which it is transmitted into region F is equal to the rate of acoustic energy entering L from Q. The thickness of region F is large enough so that the acoustic waves transmitted into the fluid, region F, are entirely absorbed and therefore no acoustic energy returns to L from F.

In the steady state, as defined above, there will be acoustic waves traveling to the right and left in regions Q and L, but only to the right in region F. The symbol, u, in FIG. 2 represents the particle displacement and the arrow attached to u is the direction of the wave of particle displacement. The wave of particle displacement is the propagation of the particle motion from one particle to a second particle adjacent to the first particle and from the second particle to the third particle and so on. For example, a thickness-shear wave is propagated in the quartz of a sensor which has the orientation known as AT-cut and in this case the particle displacement is in the direction parallel to the surface of the quartz and therefore perpendicular to the direction of the wave of particle displacement. The first subscript on u in FIG. 2 denotes the following: i for incident, t for transmitted and r for reflected. The total particle displacement wave in L is $u_{Li}+u_{Lr}$ and in Q, $u_{Qi}+u_{Qr}$.

It is well-known that in a system such as that of FIG. 2, the acoustic waves depend on a property of the material of each of the three regions called the acoustic impedance, defined as the product of density of the material and phase velocity of the wave in the material. But in this system the acoustic impedance of the three regions does not change during the process of molecular sensing, that is, as the analyte binds to the receptor. Rather, the properties of the interface between regions L and F change as the analyte binds to the receptor. The interface between regions L and F, the LF interface, means in this context both the surface of the sensor in contact with the fluid (surface of L in FIG. 2) and the interfacial region of the fluid when it is distinct from the bulk region of the fluid (region F in FIG. 2 is the bulk region in this context). For example, one of the properties of the sensor-fluid surface may be called the interfacial viscosity which is a measure of the interaction between the surface of L and the fluid molecules in contact with the surface of L. It is the change in properties of the LF interface that causes the change in distribution of acoustic waves in FIG. 2. As the analyte binds to the receptor, the wave reflected from the LF interface, $u_{Lr}$, changes and as a consequence in the steady state all waves shown in FIG. 2 will change. The acoustic waves in Q are coupled to the potential in Q by the piezoelectric effect and the potential affects the measurements made at the terminals of the sensor.

In summary the process of molecular sensing consists of the following sequence of events when the molecule to be sensed is present in the fluid.

i) Analyte binds to the receptor at the LF interface
ii) Interfacial properties of the LF interface change iii) Reflected acoustic waves from the LF interface change
iv) Acoustic waves in the quartz change
v) Potential in the quartz changes
vi) Electrical quantities measured at the terminals of the sensor change The change of measured electrical quantities is related to the concentration of the analyte which is present in the fluid.

Two electrical measurements are made at each frequency of voltage applied to the electrodes of the sensor. The measured quantities can be the voltage incident on the sensor and the voltage reflected from the sensor, called the network analysis measurements, or the voltage applied across the sensor and current flowing through the sensor, or other equivalent measurements. The two measurements made at each frequency, the measured quantities, can be combined to find the magnitude and phase of the impedance of the sensor, which are called derived quantities, or the measurements can be combined or presented in other ways.

There are several characteristic quantities which can be found from the values of the derived quantities when they are known at many different frequencies in the resonant region of the sensor. For example, if the magnitude and phase of impedance are the derived quantities, then some of the characteristic quantities, but not all, are the following: the values of minimum and maximum magnitude of impedance, the frequencies at which the magnitude of impedance is a minimum and maximum, the value of maximum phase, the frequency at which the phase is a maximum, the two frequencies at which the phase is zero (the zero-phase frequencies do not always exist), the values of minimum and maximum first derivatives with respect to frequency (the slopes) of the magnitude and phase of impedance, the frequencies at which the first derivatives are a minimum and maximum, the values of minimum, zero and maximum second derivatives with respect to frequency (the curvatures) of the magnitude and phase of impedance, and the frequencies at which the second derivatives are a minimum, zero and maximum. As the analyte binds to the receptor, the concentration of the analyte can be determined by assessing the change of one or more of the characteristic quantities.

Figure 3:
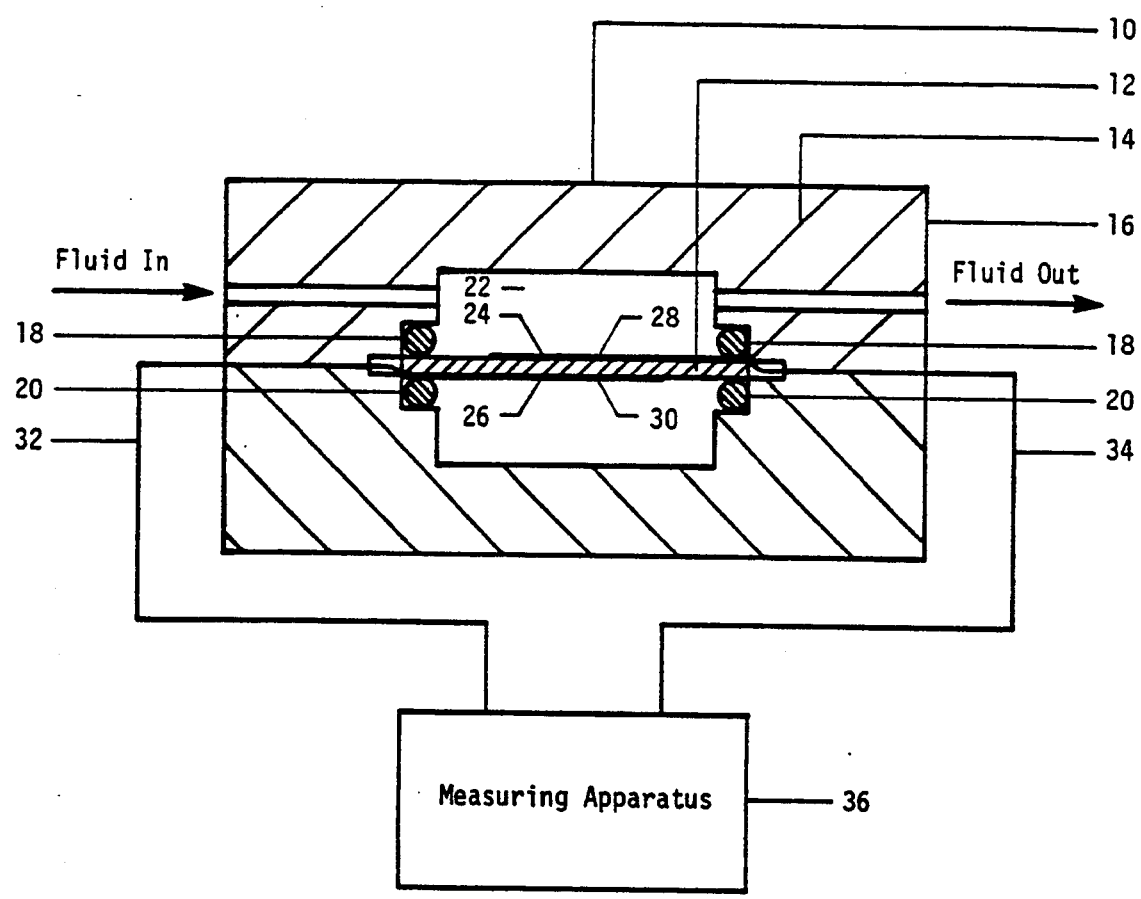
FIG. 3 is a section through the measuring apparatus of this invention using a sensing device of FIG. 1.

The essential features of the measurement method are shown in FIG. 3 which is not drawn to scale. FIG. 3 is a cross-sectional view of the device 10 perpendicular to the plane of the sensor 12 and through the center of the sensor 12. The broadly cross-hatched region 14 is a flow-through cell 16 in which the sensor is clamped between two O-rings 18 and 20. The fluid 22 (liquid or gas) is in contact with one side 24 of the sensor in FIG. 3, but the fluid could make contact with both sides 24 and 26 of the sensor. The electrodes 28, 30 on each face of the sensor are connected by electrical conductors 32, 34 to the measuring apparatus 36.

This invention also relates to applications of the molecular sensing process of which the receptor or analyte or both are biomolecules. The biomolecule may be one or more of the following:

i) one strand or part of a strand of a DNA molecule;
ii) an antibody or fragment thereof;
iii) an antigen or one or more determinants thereof;
iv) a bioreceptor.

Examples of applications follow which are to be understood as illustrative of the scope of the applications of the process and which are understood to be non-limiting with respect to the appended claims.

EXAMPLES OF APPLICATIONS

1. DNA Sensor

The analyte, A in FIG. 1, is single-strand DNA. The receptor, R in FIG. 1, is complementary DNA, strands of DNA which are complementary to the analyte. The electrode, M in FIG. 1, is gold. The coating, C in FIG. 1, consists of a thiol monolayer self-assembled on the gold and a linking agent.

The DNA sensor detects interfacial nucleic acid hybridization by the acoustic reflection process. An unmodified piezoelectric quartz crystal with gold electrodes is cleaned by plasma etching. The crystal is then immersed in methanol which contains 2.2% W/V 11-mercaptoundecanoic acid (MUA) for twenty-four hours. The crystal is washed with small amounts of acetone and dried in a stream of clean nitrogen.

Single-strand DNA is covalently linked to the carboxylic acid functionalities of MUA. This is achieved by exposing the crystal with thiol on its surface to a 1:1 solution of 10 mg/mL 1-ethyl-3-(3-dimethylaminopropyl)-carbodiimide hydrochloride (DEC) and 1 mg/mL denatured DNA (which had been heated to 100° C. for 20 minutes) for twelve hours at 5° C. The crystal is allowed to warm to room temperature and then is washed extensively with distilled water for five minutes and dried.

The amount of DNA immobilized on the sensor surface can be determined by first removal with EDTA solution at 100° C. followed by measurement of UV absorbance at 260 nm.

The sensor is incorporated into the measurement system of the acoustic reflection process and then exposed to solutions of complementary single-strand DNA in EDTA and Tris buffer solution of 42° C.

The magnitude and phase of impedance is measured at many different frequencies in the resonant region of the sensor and several characteristic quantities are found from these experimental results. For example, the frequency of maximum phase changes by an order of magnitude of 1000 Hz when the complementary single-strand DNA is present in solution.

2. Sensor for Drug-Receptor Interactions

The analyte, A in FIG. 1, is a bio-receptor from a cell, identical molecules, usually proteins, to which a drug is designed to bind. The receptor, R in FIG. 1, is an agonist, molecules that bind to the analyte when it is in the cell and thereby trigger a cascade of biochemical reactions in the cell. The word, receptor, has two distinct meanings in this example: receptor, alone, means the molecules immobilized on the surface of the sensor (R in FIG. 1) which bind to the analyte, and bio-receptor in the phrase, bio-receptor from a cell, means the analyte.

The sensor for drug-receptor interactions is incorporated in a flow injection analysis (FIA) system, which is capable of stop-flow measurements. A particular agonist for the bio-receptor from a cell is immobilized on the sensor surface. In the FIA system, the bio-receptor from a cell is introduced in a buffer liquid over the sensor surface. Kinetic measurements by the acoustic reflection process are made of the binding of the bio-receptor from a cell to the agonist until equilibrium is reached. At equilibrium, a certain fraction of the agonist will be bound to the bio-receptor from a cell. Then a drug, molecules which also bind to the bio-receptor from a cell, is introduced in a liquid over the sensor surface and measurements are made. Some of the occupied agonist, the agonist which is bound to the bio-receptor from a cell, will be displaced by the drug. Therefore, in the presence of the drug the fraction of occupied agonist will be less than the fraction in the absence of the drug. This procedure constitutes a competitive binding assay of drug-receptor interactions using the acoustic reflection process.

Characteristic quantities are found from the experimental results of the acoustic reflection process, as in the DNA sensor application for example.

3. Sensor for Immunochemical Diagnostics

The analyte, A in FIG. 1, is an antigen which is the subject of an assay. The receptor, R in FIG. 1, is an antibody which specifically binds to the analyte.

The array described above requires linking of an antibody, for example, IgG, to the surface of the gold electrodes of the BAW sensor. Two general methods are used for this purpose:

i) A film of protein A is deposited on the gold electrode surface by placing drops of protein A solution on the electrode followed by evaporation. The protein A film/sensor combination is then exposed to a buffered solution of antibody. The antibody binds to the protein A film.

ii) A film of polyacrylamide gel is placed on the electrode surface. The thickness of the gel film is about 50 μm. After immersion of the gel in glutaraldehyde solution for several hours at 40° C. followed by copious washing with water, the polymer is treated with a solution of antibody for twenty-four hours at 2° C. Unreacted glutaraldehyde functionalities are then neutralized with L-lysine solution. After washing the sensor is stored under 0.1% sodium oxide solution and kept in the dark.

In a particular immunoassay, the BAW-antibody combination is allowed to interact with the antigenic species. Characteristic quantities are found from the experimental results of the acoustic reflection process, as in the DNA sensor application for example.

Although preferred embodiments of the invention are described herein in detail, it will be understood by those skilled in the art that variations may be made thereto without departing from the spirit of the invention or the scope of the appended claims.

We claim:

1. A passive process for specifically sensing analyte molecules in a fluid by reflection of bulk acoustic waves from a sensing surface of a bulk acoustic wave quartz sensing device to which analyte molecules bind, said sensing device comprising a thin quartz plate having opposing surfaces, a thin electrically conductive means on each of the two opposing surfaces, wherein at least one of said conductive means is a sensing surface and supports a plurality of receptors for which analyte molecules have an affinity, said process comprising:

i) contacting a fluid in which analyte molecules are suspected with said sensing surface;

ii) applying a voltage to said bulk acoustic wave quartz sensing device to produce an electromagnetic field in said quartz sensing device, the applied voltage being one of a sinusoidal time-varying voltage or other periodically or non-periodically varying voltage to generate acoustic waves in said quartz device, directing such acoustic waves at said sensing surface whereby acoustic waves are reflected from said sensing surface; and iii) detecting a change in a characteristic of acoustic waves reflected from said sensing surface due to analyte molecules binding said receptors, said change in the reflected acoustic wave characteristic being measured by said conductive means thereby detecting a change in said electromagnetic field which is related to the amplitude and phase of the reflected acoustic waves, said conductive means directly detecting said change in electromagnetic field by making two electrical measurements at one frequency or at each of one or more than one frequency of sinusoidal voltage applied to the sensing device, or equivalent measurements for applied voltages varying non-sinusoidally with time, the measured electrical quantities being the incident voltage on said sensing device and reflected voltage from said sensing device, or applied voltage across said sensing device and current flowing through said sensing device, or other equivalent measured quantities.

2. A process as defined in claim 1, in which the acoustic waves are reflected by both the sensing surface and an interfacial region of fluid in contact with said sensing surface, when one or more properties of the interfacial region vary as the analyte binds said receptors.

3. A process of claim 2 wherein said receptor on said sensing surface is specific for a biomolecule.

4. A process of claim 1 wherein said receptor on said sensing surface is specific for a biomolecule.

5. A process of claim 4 wherein said biomolecule is one strand or part of one strand of a DNA molecule.

6. A process of claim 4 wherein said biomolecule is an antibody or fragment thereof.

7. A process of claim 4 wherein said biomolecule is an antigen or one or more determinants thereof.

8. A process of claim 4 wherein said biomolecule is a bio-receptor.

9. A process as defined in claim 1 in which the fluid is a liquid.

10. A process of claim 9 wherein said biomolecule is one strand or one part of a strand of a DNA molecule.

11. A process of claim 9 wherein said biomolecule is an antibody or fragment thereof.

12. A process of claim 9 wherein said biomolecule is an antigen or one or more determinants thereof.

* * * * *